(12) United States Patent
Szczykutowicz

(10) Patent No.: US 11,071,506 B1
(45) Date of Patent: Jul. 27, 2021

(54) X-RAY IMAGING DEVICE PROVIDING ENHANCED SPATIAL RESOLUTION BY ENERGY ENCODING

(71) Applicant: Wisconsin Alumni Research Foundation, Madison, WI (US)

(72) Inventor: Timothy Peter Szczykutowicz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/860,415

(22) Filed: Apr. 28, 2020

(51) Int. Cl.
*A61B 6/00* (2006.01)

(52) U.S. Cl.
CPC .................. *A61B 6/4266* (2013.01)

(58) Field of Classification Search
CPC ................................... A61B 6/4266
See application file for complete search history.

(56) References Cited

U.S. PATENT DOCUMENTS

| | | | | |
|---|---|---|---|---|
| 4,361,901 A * | 11/1982 | Daniels | ..................... | A61B 6/02 257/10 |
| 5,570,403 A * | 10/1996 | Yamazaki | ............... | A61B 6/032 378/19 |
| 6,246,747 B1 * | 6/2001 | Wear | ..................... | G01N 23/083 378/98.11 |
| 6,449,334 B1 * | 9/2002 | Mazess | ................. | G01N 23/083 378/53 |
| 7,120,222 B2 * | 10/2006 | Hoffman | ............... | A61B 6/4007 378/5 |
| 9,490,099 B2 * | 11/2016 | Mackie | ................ | A61B 6/4007 |
| 10,743,826 B2 * | 8/2020 | Cao | ........................ | A61B 6/4275 |
| 2004/0066978 A1 * | 4/2004 | Nanbu | ..................... | G06T 5/002 382/261 |
| 2004/0234031 A1 * | 11/2004 | Francke | ................. | A61B 6/405 378/98 |
| 2004/0264628 A1 * | 12/2004 | Besson | ................ | A61B 6/4241 378/5 |
| 2005/0069086 A1 * | 3/2005 | Deych | .................... | A61B 6/542 378/112 |
| 2005/0276373 A1 * | 12/2005 | Ying | ..................... | G01N 23/046 378/7 |
| 2006/0023844 A1 * | 2/2006 | Naidu | ..................... | G01T 1/185 378/210 |
| 2006/0072703 A1 * | 4/2006 | Naidu | .................. | G01V 5/0008 378/101 |
| 2007/0133744 A1 * | 6/2007 | Bijjani | .................... | A61B 6/032 378/57 |
| 2009/0052615 A1 * | 2/2009 | Ribbing | ................. | A61B 6/032 378/9 |
| 2009/0147919 A1 * | 6/2009 | Goto | ....................... | A61B 6/482 378/86 |
| 2009/0147922 A1 * | 6/2009 | Hopkins | ................. | G21K 1/062 378/140 |
| 2010/0014628 A1 * | 1/2010 | Kadomura | ............. | A61B 6/032 378/4 |
| 2010/0172464 A1 * | 7/2010 | Pavlovich | ............ | A61B 6/4028 378/9 |

(Continued)

*Primary Examiner* — Blake C Riddick
(74) *Attorney, Agent, or Firm* — Boyle Fredrickson, S.C.

(57) ABSTRACT

A high-resolution x-ray imaging system encodes spatial information into x-ray energy by an encoding filter which changes the x-ray energy sensitivity of each detector at different portions of the detector. Acquiring successive images at different energies allows the fluence at different portions of a single detector to be isolated providing effective sub detector resolution.

19 Claims, 4 Drawing Sheets

(56) References Cited

U.S. PATENT DOCUMENTS

| | | | | |
|---|---|---|---|---|
| 2011/0216883 | A1* | 9/2011 | Tsukamoto | A61B 6/4241 378/62 |
| 2012/0219106 | A1* | 8/2012 | Stierstorfer | A61B 6/032 378/15 |
| 2012/0236987 | A1* | 9/2012 | Ruimi | A61B 6/4028 378/19 |
| 2013/0022168 | A1* | 1/2013 | Cho | A61B 6/482 378/62 |
| 2013/0101082 | A1* | 4/2013 | Jordan | A61N 5/1037 378/19 |
| 2015/0238160 | A1* | 8/2015 | Flohr | A61B 6/032 378/8 |
| 2015/0260875 | A1* | 9/2015 | Schafer | G01V 5/0008 378/4 |
| 2015/0272522 | A1* | 10/2015 | Robinson | A61B 6/482 378/5 |
| 2015/0331115 | A1* | 11/2015 | Nelson | G01T 1/1611 250/363.03 |
| 2016/0220207 | A1* | 8/2016 | Jouhikainen | A61B 6/4021 |
| 2017/0023498 | A1* | 1/2017 | Worsted | A61B 6/52 |
| 2017/0115406 | A1* | 4/2017 | Li | G01T 1/2018 |
| 2017/0128029 | A1* | 5/2017 | Penfold | A61N 5/1069 |
| 2017/0150934 | A1* | 6/2017 | Bennett | A61B 6/037 |
| 2018/0136340 | A1* | 5/2018 | Nelson | A61B 6/4241 |
| 2018/0136344 | A1* | 5/2018 | Nelson | A61B 6/4233 |
| 2019/0317227 | A1* | 10/2019 | Nelson | A61B 6/032 |
| 2019/0374182 | A1* | 12/2019 | Karim | A61B 6/505 |
| 2020/0069271 | A1* | 3/2020 | Maalej | H01J 35/101 |
| 2020/0222016 | A1* | 7/2020 | Pan | A61B 6/469 |
| 2020/0233100 | A1* | 7/2020 | Rothschild | G01T 1/2006 |
| 2020/0323502 | A1* | 10/2020 | Kojima | A61B 6/4266 |
| 2020/0364909 | A1* | 11/2020 | Bai | G01T 1/2985 |

\* cited by examiner

X-RAY IMAGING DEVICE PROVIDING ENHANCED SPATIAL RESOLUTION BY ENERGY ENCODING

STATEMENT REGARDING FEDERALLY SPONSORED RESEARCH OR DEVELOPMENT

—

CROSS REFERENCE TO RELATED APPLICATION

—

BACKGROUND OF THE INVENTION

The present invention relates to x-ray imaging devices for industrial and medical use and in particular to a device providing improved spatial resolution.

The spatial resolution of an x-ray imaging machine determines the machine's ability to resolve small features in an imaged object, for example, cracks in a metal casting being inspected on an industrial x-ray machine, or the fine structure of bones in the ear of a human patient in medical imaging.

Generally, the resolution of the x-ray imaging machine is limited by the size of the x-ray focal spot (an area over which x-rays can be considered to emanate) and the size of each detector element receiving the x-rays after they pass through the object being imaged.

Focal spot size tends to be strongly linked to x-ray fluence (photons per unit time) and for this reason reductions in focal spot size are constrained by the offsetting increase in exposure times that are required to provide a sufficiently low noise image. The alternative of maintaining constant fluence with a smaller focal spot can lead to anode melting as increasing amounts of energy are concentrated in a smaller area.

Much of the improvement in x-ray imaging resolution has been by decreasing the size of the detector elements. X-ray detectors used for early x-ray computed tomography (CT) machines had a detector size with approximately 3 mm spacing which has steadily decreased to a common spacing of 0.5 mm with a few examples of detector spacing as low as 0.25 mm.

Reduction of detector spacing below current levels is difficult for a number of reasons including a substantial reduction of "geometric efficiency" caused by increasing the proportion of the areas of detector "gutters" (representing material isolating the detectors from each other) compared to usable detector area. In addition, there are substantial manufacturing difficulties associated with smaller detector sizes including obtaining adequate yields of detector arrays with many more detector elements and the difficulty and cost of providing electrical interconnections to many more detector elements.

One method of creating the benefit of smaller detector sizes without actually reducing the size of the detector elements places a mask or comb over the detector elements that block all but a small portion of the active detector imaging area. This approach provides higher resolution imaging but at the expense of wasting significant x-ray energy (of particular concern in medical imaging were dose should be limited) and increased signal noise.

SUMMARY OF THE INVENTION

The present invention provides a way of increasing the spatial resolution of an array of detector elements, without a change in focal spot area or detector spacing, by encoding x-ray energy into spatial information providing spatial resolution at a scale smaller than the detector element spacing. In one example, the invention may provide a filter with an energy dependent transmission that covers only a portion of each detector. Acquiring successive images with these modified detector elements, using different x-ray energies, allows the x-ray fluence received by the different portions of the detector to be isolated producing effective sub-pixel spacing resolution (where pixel is defined by the size of the detector element).

More specifically, the present invention provides an x-ray imaging device having a multi-energy x-ray source providing first and second x-rays with different x-ray energies, the energies describing a distribution of energy of x-ray photons of the first and second x-rays. A multi-element x-ray detector is positioned to receive the first and second x-rays from the multi-energy x-ray source after passage through an object to be imaged to provide an x-ray fluence output for each element. The invention further employs an x-ray energy filter positioned with respect to the x-ray energy source and the multi-element x-ray detector to provide a first and second different response to at least one of the received first and second x-rays at different first and second portions of each element. A controller communicates with the multi-energy x-ray source and multi-element x-ray detector to: (a) acquire a first and second x-ray image of x-ray fluence outputs of each of the elements of the multi-element x-ray detector at the first and second energy; and to (b) process the first and second x-ray images to provide independent fluence measurements for the first and second portions of each element of the multi-element x-ray detector.

It is thus a feature of at least one embodiment of the invention to provide finer spatial resolution from an x-ray detector by using a filter to encode x-ray energy into spatial information. The filter allows the invention to differentiate x-ray fluence received by different portions of the detector element.

The controller may output an image having multiple, independent pixels for each detector element It is thus a feature of at least one embodiment of the invention to provide higher resolution images without the inefficiencies of masks or combs that fully block x-rays. The filter used by the present invention allows the detector elements to receive and measure x-rays over the entire active area of the element.

The processing of the first and second x-ray images uses a change in fluence detected at given elements of the multi-element x-ray detector between different x-ray energies to deduce the relative proportion of x-ray fluence being received at the first and second portions of each element.

It is thus a feature of at least one embodiment of the invention to determine x-ray fluence in different filtered portions of a detector element using an evaluation of a difference in fluence with changes in energy.

The multi-energy x-ray source may provide at least a first, second, third, and fourth different energy and the controller may acquire a first, second, third, and fourth x-ray image of x-ray fluence outputs of each of the elements of the multi-element x-ray detector at the first, second, third, and fourth energy, respectively, to determine independent fluence measurements for the first and second portions of each element of the multi-element x-ray detector.

It is thus a feature of at least one embodiment of the invention to accommodate the imaging of soft tissue and the like where there are both Compton scattering and photoelectric attenuation affects. By acquiring at least four images, these additional unknown factors may be accounted for in extracting the first and second portions.

The multi-element x-ray detector may provide elements distributed in two dimensions and the x-ray energy filter may create a first, second, third, and fourth different response to a received x-ray's fluence at corresponding first, second, third, and fourth portions of each element. In this case, the controller acquires a first, second, third, and fourth x-ray image of x-ray fluence outputs of each of the elements of the multi-element x-ray detector at the first, second, third, and fourth energy; and processes the first, second, third, and fourth x-ray images to provide independent fluence measurements for the first, second, third, and fourth portions of each element of the multi-element x-ray detector.

It is thus a feature of at least one embodiment of the invention to provide for increased spatial resolution in two-dimensional detector arrays.

The multi-energy x-ray source may switchably provide the first and second x-rays at different times and/or may provide monochromatic or polychromatic x-rays. The x-rays provided by the multi-energy x-ray source may be either megavoltage or kilovoltage x-rays. The multi-element x-ray detector may be an energy discriminating detector that can distinguish between different x-ray energies or may provide no energy discrimination. Likewise the multi-element x-ray detector may be either a direct detector having a single electrode associated with each detector element or indirect detectors having a single photo sensor associated with each detector.

It is thus a feature of at least one embodiment of the invention to provide a system that can be flexibly used with many different imaging architectures.

The x-ray filter may be an absorbing material positioned between the multi-energy x-ray source and the object to be imaged to intercept only a portion of the x-rays received by each given element of the multi-element x-ray detector.

It is thus a feature of at least one embodiment of the invention to permit filtration to be done near the x-ray source without modification of the detector and without completely blocking x-ray energy.

Alternatively or in addition, the x-ray filter may be an absorbing material placed between the object to be imaged and the multi-element x-ray detector and covering only a portion of each element of the multi-element x-ray detector.

It is thus a feature of at least one embodiment of the invention to provide a simple filter design that can be affixed to current multi-element detectors, for example, in the manner currently used for detector masks or comb filters or the like. It is a further object of at least one embodiment to reduce blurring of the filter effect on the detector elements caused by proximity of the filter to the finite-sized x-ray focal spot from which x-rays emanate.

In one embodiment, the x-ray filter may provide the first and second different response by means of a first and second material converting x-ray energy to light energy positioned at different portions of each detector element.

It is thus a feature of at least one embodiment of the invention to provide the necessary filter characteristics (favoring some x-ray energies over others) through a selection of converter material rather than by a blocking of x-rays, the former which may offer higher detection efficiencies to the extent that x-rays are not blocked.

The multi-element x-ray detector may provide a first, second, third, and fourth different response to a received x-ray's fluence at corresponding first, second, third, and fourth portions of each element.

It is thus a feature of at least one embodiment of the invention to provide an arbitrary increase in spatial resolution not necessarily linked to a two-dimensional detector array but possibly along a single axis.

In one embodiment, the multi-element x-ray detector may provide elements distributed only in a single dimension and the first and second portions of each element may be displaced with respect to the third and fourth portions of each element along the first axis substantially perpendicular to an axis of the x-rays and wherein the first and third portions are displaced with respect to the second and fourth portions along a second axis substantially perpendicular to the first axis and the axis of x-rays.

It is thus a feature of at least one embodiment of the invention to allow increases in spatial resolution in two dimensions on a one-dimensional detector array used, for example, for helical or multislice scanning common to tomographic or projection slot scanning applications.

The controller may further processes the first and second x-ray images to distinguish between first and second basis materials of the object to be imaged for each element of the multi-element x-ray detector.

It is thus a feature of at least one embodiment of the invention to permit "spectral" or "dual energy" imaging simultaneously with a boosting of image resolution.

These particular objects and advantages may apply to only some embodiments falling within the claims and thus do not define the scope of the invention.

DETAILED DESCRIPTION OF THE PREFERRED EMBODIMENT

Figure 1:
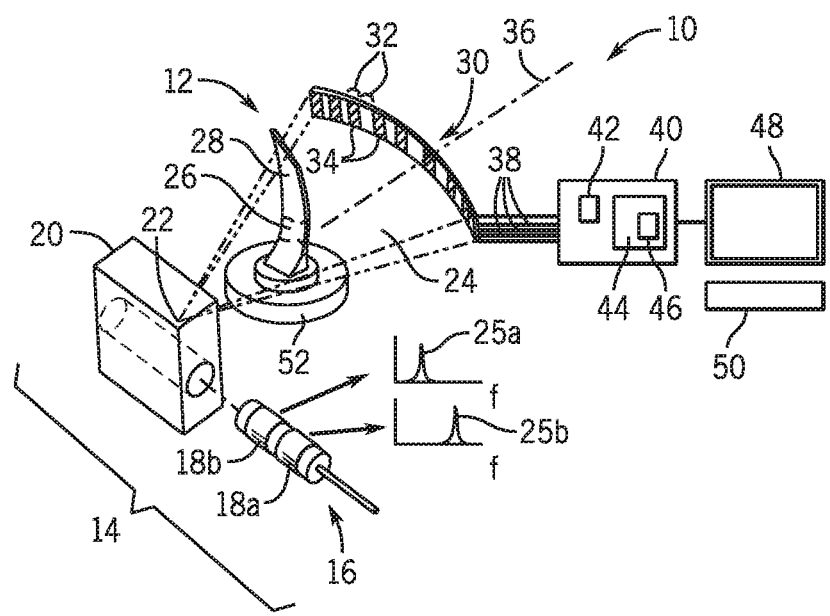
FIG. 1 is a simplified perspective view of an industrial x-ray machine suitable for use with the present invention showing a fan beam of radiation received by a one-dimensional detector array.

Referring now to FIG. 1, an x-ray imaging device 10 suitable for use for industrial inspection of an imaged object 28 may provide a multi-energy x-ray source 14, for example, providing an insert 16 of naturally radioactive materials 18a and 18b, such as Cesium-137 and Iridium-192. The naturally radioactive materials 18 may be accompanied by filters to produce essentially monochromatic x-ray energies.

The radioactive materials 18 in the insert 16 may be separated by shielding spacers to form a cylinder that can slide within a bore of a shielding block 20 to provide a switchable multi-energy x-ray source 14. By aligning particular ones of the materials 18 with an aperture 22 in one wall of the bore, a fan beam of x-ray radiation 24 may be formed providing either of two substantially monochromatic energies 25a and 25b, respectively, for example, 0.66 million electron volts and 0.38 million electron volts.

The fan beam of x-ray radiation 24 may be positioned to illuminate a slice 26 of an imaged object 28 or to inspect interior features of the imaged object 28, for example, to inspect a casting 12 for cracks, voids or the like. X-rays of the fan beam 24, passing through the imaged object 28, are received by a one-dimensional detector array 30 (shown in exaggerated scale) comprised of multiple detector elements 32 arrayed along a direction perpendicular to a central axis 36 of the fan beam, for example, at a constant radius around the aperture 22. Together the central axis 36 and the axis of the detector elements 32 define a fan beam plane along which the broadest extent of the fan beam of x-ray radiation 24 lies. More generally, the invention contemplates x-rays having other beam shapes, such as cone beams, and other detector shapes, such as flat detectors, as will be recognized by those of ordinary skill in the art from the following discussion.

In this embodiment, each of the detector elements 32 is partially covered by a filter material 34, as will be discussed below. For example, the filter material 34 may cover one half of the area of each detector element 32.

Each of the detector elements 32 provides an independent fluence signal measuring the fluence of x-rays received over an entire active area of the detector element 32. These fluence signals may be conducted over signal lines 38 to be received by a controller 40, for example, having one or more processors 42 communicating with computer memory 44 holding a stored program 46. The stored program 46 will provide for a processing of fluence information from the signal lines 38 as will be discussed below.

The controller 40 may further communicate with the display 48 for outputting text and/or graphics (such as projection or tomographic images) and user input device 50, for example, a keyboard mouse or the like for providing control commands for controlling the execution of the stored program 46 on the controller 40.

In one embodiment, a tomographic image may be acquired using the x-ray imaging device 10 of FIG. 1 by rotating the imaged object 28, for example, on a turntable 52 with respect to the axis 36 and at various points in the rotation acquiring an image of the imaged object 28 consisting of contemporaneous fluence data from each of the detector elements 32.

As will be discussed below, the x-ray imaging device 10 may alternatively acquire a standard projection image of the imaged object 28 by using a cone beam of x-rays (rather than the depicted fan beam of x-ray radiation 24) and a two-dimensional detector array as will be discussed below. In this case, the imaged object 28 may remain stationary to obtain a standard projection image. The two-dimensional detector array may also be used for cone beam tomographic reconstruction by rotating the imaged object as before.

Figure 2:
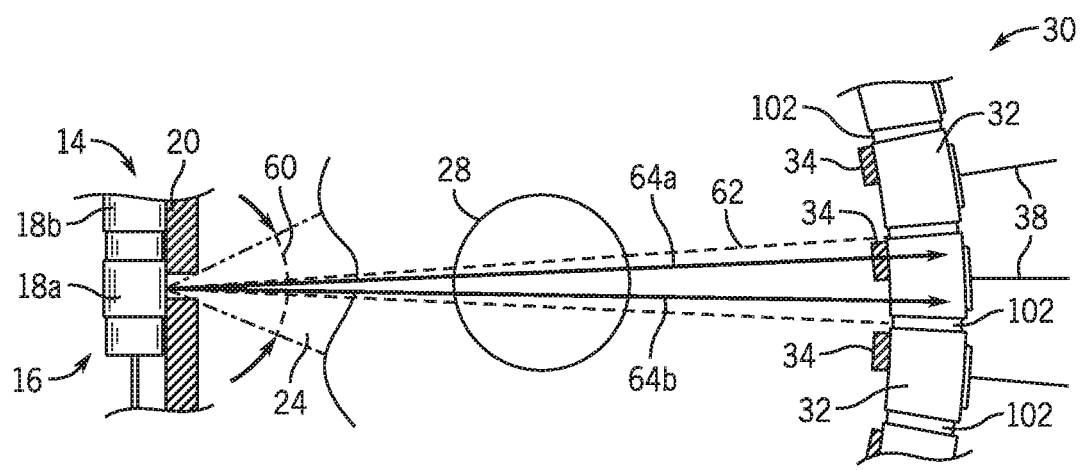
FIG. 2 is a top plan fragmentary view of FIG. 1 showing a filter mask positioned on the detector array.

Referring now also to FIG. 2, the fan beam of x-ray radiation 24 may have an angular extent 60 in the plane of the detector array 30 that may be divided into multiple rays 62 being a fraction of that angular extent 60. Generally, the angular extent of the rays 62 will match an angle of the fan beam of x-ray radiation 24 subtended by a single detector element 32. Each such ray 62 may be further divided into a left sub-ray 64a and a right sub-ray 64b (here represented by their centerlines) which in one embodiment divide each ray 62 in half across the fan beam plane. One sub-ray 64a may be received by a given detector element 32 after passing through a filter material 34 while the other sub-ray 64b may be received by the given detector element 32 directly. The filter material 34 provides an attenuation of specific energies of x-rays to desirably transmit different x-ray fluences having different attenuation profiles (attenuation is a function of energy) in different portions of the detector element 32 and further depending on whether the radioactive material 18a or 18b is being used. The filter material 34, for example, may be a thin sheet of material such as aluminum positioned over each given detector element 32 of the detector array 30 and positioned to intercept sub-ray 64a for the given detector element 32 while providing an opening to pass sub-ray 64b to the given detector element 32 without attenuation.

Figure 4:
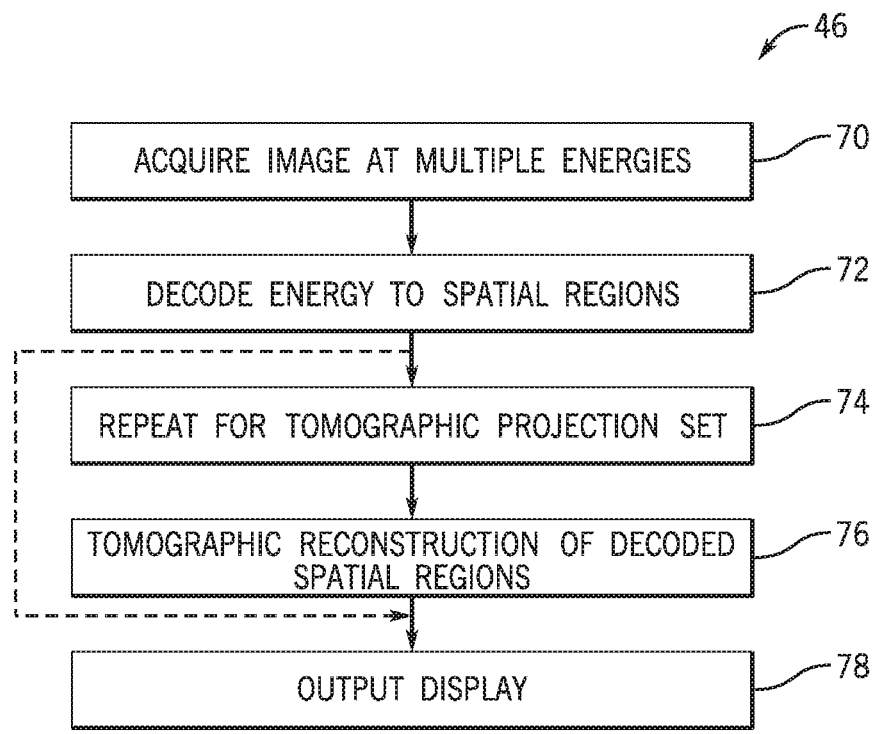
FIG. 4 is a flowchart showing steps of processing the data collected from the devices in FIGS. 1 and 3.

As positioned, the filter material 34 encodes spatial information (whether the detected x-ray fluence is from sub-ray 64a or 64b) into an energy of the incident x-rays allowing decoding of that spatial information by the controller 40. Referring also to FIG. 4, this decoding process may be performed by the controller 40 executing program 46. At a first process block 70 of the program 46, the controller 40 acquires multiple images of the imaged object 28 at different energies. Each image will be a collection of fluence values from each element 32 taken during a common exposure time. In the case of a tomographic scan using the x-ray imaging device 10 of FIG. 1, pairs of images may be taken at each given angle of the imaged object 28 with one image of the pair using radioactive material 18a and the other image of the pair using radioactive material 18b. These image pairs may be acquired either by switching between the radioactive materials 18 at each angular position of the imaged object 28 or by making successive rotations of the imaged object 28 switching between the radioactive materials 18 between the different rotations.

At process block 72, each of these imaging pairs is processed to decode additional spatial resolution from the energy information associated with each image of the pair. In this regard, the fluence signal from each detector element 32 without filtration of the filter material 34 may be represented by the equation:

$$S_{i,j} = \Omega_i \omega_j e^{-\int d\vec{l}\, \mu(x,y,E)} \tag{1}$$

where:

$S_{i,j}$ is the fluence detected at each element 32 for given x-ray energy spectrum i and a given detector sensitivity j;

$\Omega_i$ is the energy spectrum incident onto the imaging object which will be different for each image of an image pair and for the case of a monochromatic beam will be a delta function at the monochromatic beam energy;

$\omega_j$ is the sensitivity of the imaging element 32 at the particular monochromatic energy defined by $\Omega i$ and for the sensitivity denoted by j;

E is the energy which in the case of a monochromatic beam would be equal to the energy of the incident spectra $\Omega_i$, and ∫dl$\mu$(x,y,E) is a line integral along a given sub-ray 64 defined by the position vector $\vec{l}$ being a function of the material of the imaged object 28 along that line (in an x-y plane perpendicular to the x-ray energy propagation) at the particular x-ray energy E which for a monochromatic spectrum $\Omega_i$ is equal to the monochromatic energy of $\Omega_i$. This line integral represents the attenuation of the x-rays by the material of the imaged object 28.

The fluence signals received by an element 32 having the filtration described above for two different energy levels $\Omega i$ with a detector response $\omega$ operated in a constant discrimination mode with an energy dependency will then be equal to:

$$S_1 = F^R \Omega_1 \omega_1 e^{-\int d\vec{l}^R \mu(x,y,E)} + F^L \Omega_1 \omega_1 e^{-\int d\vec{l}^L \mu(x,y,E)} \quad (2)$$

$$S_2 = F^R \Omega_2 \omega_2 e^{-\int d\vec{l}^R \mu(x,y,E)} + F^L \Omega_2 \omega_2 e^{-\int d\vec{l}^L \mu(x,y,E)} \quad (3)$$

where $F^R$, $F^L$ are the effective filtering for the left and right sub-rays 64a and 64b, that is the effect of the filter material 34 in attenuating the x-rays and $\Omega_1$ and $\Omega_2$, the two different x-ray energies employed in collecting these images.

When the imaged object 28 is a material such as metal and the imaging spectra f are high energy (e.g., megavoltage range), the attenuation of the line integral will mostly be driven by Compton scattering. The line integrals over, ∫d $\vec{l}\mu$(x,y,E) then each can be parameterized using just the Compton effect and equations (2) and (3) provide two equations with two unknowns (the line integrals for the right and left sub-rays 64, respectively). This allows the line integrals, or the intensities, to be separately determined for different sub-rays 64 of a single detector element 32 by simple algebraic manipulation.

These separate line integrals can then be mapped to sub pixels in a resulting image, each subpixel providing an independent brightness value for different portions of a single detector element 32 which would normally map to a single image pixel. The result can be processed using image processing algorithms and may also be displayed as an image providing higher spatial resolution per process block 78, this image providing twice the spatial resolution than would be expected from the detector spacing. Normally when a projection image is obtained in this manner, a two-dimensional detector array 30 will be employed, or a one-dimensional detector array such as is shown in FIG. 1 will be scanned vertically to provide a two-dimensional projection image.

If a tomographic image is being acquired, then after the decoding step of process block 72 for each image pair, multiple images at different angles about the imaged object 28 are taken per process block 74. These images may then be reconstructed per process block 76 using standard tomographic reconstruction algorithms such as filtered back projection. These reconstruction algorithms operate using the increased resolution decoded regions obtained as described above. At process block 78, the tomographic image rather than the projection image can be provided.

Figure 3:
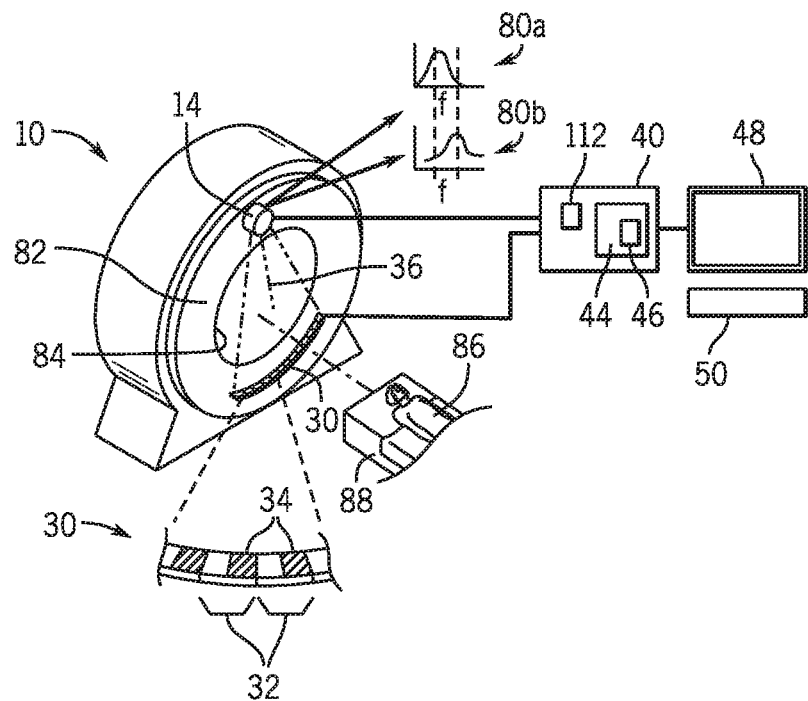
FIG. 3 is a figure similar to that of FIG. 1 showing a multi-energy computed tomography machine suitable for practice of the present invention.

Referring now to FIG. 3, it will be appreciated that the invention may be advantageously applied to standard medical imaging, for example, using a dual energy CT machine capable of producing a first polychromatic energy spectrum 80a and second energy spectrum 80b having different energy profiles, for example, using an x-ray tube as the x-ray source 14. As is generally understood in the art, the x-ray CT machine may provide for a rotatable gantry 82 supporting the x-ray source 14 and detector array 30 about an opening 84 sized to receive a patient 86 and patient support table 88, the latter of which may translate along an axis perpendicular to the fan beam axis 36 through the opening 84. As is understood in the art, the detector array 30 may be a one-dimensional detector array used with a fan beam or two-dimensional detector array that may be employed by a cone beam.

Referring again to FIG. 4, when imaging soft tissue typical in a CT medical scan, the steps taken to deduce spatial information at process block 72 are slightly more complicated because the attenuation of the x-rays will be significantly affected both by Compton scattering and by photoelectric effects, these two attenuation mechanisms adding additional unknowns into the equations discussed above and requiring additional images to be acquired at additional different energies. Further, a dual energy CT x-ray system of this kind will typically produce a polychromatic x-ray beam. Under these circumstances, equation (1) becomes:

$$S_{i,j} = \int_0^{E_{max}} dE [F(E)^L \Omega(E)_i \omega(E)_j e^{-\int d\vec{l}^L \mu(x,y,E)} + F(E)^R \Omega(E)_i \omega(E)_j e^{-\int d\vec{l}^R \mu(x,y,E)}] \quad (4)$$

where F, $\Omega$, $\omega$ are now more complex functions of energy (E) than in the monochromatic case discussed above and $E_{max}$ is the maximum photon energy in the incident spectrum $\Omega$. The line integrals in the above equation (4) can be decomposed into:

$$\int d\vec{l}^R \mu(x,y,E) = PE(E) \int d\vec{l}^R A(x,y) + CE(E) \int d\vec{l}^R B(x,y) \quad (5)$$

$$\int d\vec{l}^L \mu(x,y,E) = PE(E) \int d\vec{l}^L A(x,y) + CE(E) \int d\vec{l}^L B(x,y) \quad (6)$$

where:

PE(E) is attenuation caused by the photoelectric effect as a function of energy of the polychromatic x-rays; and CE(E) is the attenuation caused by Compton scattering as a function of energy of the polychromatic x-rays.

In this case there are four unknown values being the attenuation caused in the left sub-ray 64a by Compton scattering and photoelectric effect, respectively, and the attenuation caused in the right sub-ray 64b caused by Compton scattering and photoelectric effect. These unknowns can be numerically solved for using four independent equations taken at four different energy levels as follows:

$$S_1 = \int_0^{E_{max}} dE \Omega(E)_1 \omega(E) [F(E)^L e^{-\int d\vec{l}^L \mu(x,y,E)} + F(E)^R e^{-\int d\vec{l}^R \mu(x,y,E)}] \quad (7)$$

$$S_2 = \int_0^{E_{max}} dE \Omega(E)_2 \omega(E) [F(E)^L e^{-\int d\vec{l}^L \mu(x,y,E)} + F(E)^R e^{-\int d\vec{l}^R \mu(x,y,E)}] \quad (8)$$

$$S_3 = \int_0^{E_{max}} dE \Omega(E)_3 \omega(E) [F(E)^L e^{-\int d\vec{l}^L \mu(x,y,E)} + F(E)^R e^{-\int d\vec{l}^R \mu(x,y,E)}] \quad (9)$$

$$S_4 = \int_0^{E_{max}} dE \Omega(E)_4 \omega(E) [F(E)^L e^{-\int d\vec{l}^L \mu(x,y,E)} + F(E)^R e^{-\int d\vec{l}^R \mu(x,y,E)}] \quad (10)$$

where each of the signals $S_1$ to $S_4$ is acquired at different energies using the same detector response, typically, but not necessarily, ranging to different energy spectra defined by $\Omega_1$, $\Omega_2$, $\Omega_3$, and $\Omega_4$. The four unknowns may be resolved through these four independent equations by standard algebraic techniques.

Figure 5:
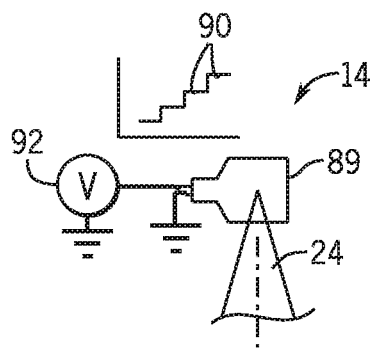
FIG. 5 is a block diagram of a first embodiment of a multi-energy x-ray source employing different anode cathode voltages.

Referring now to FIG. 5, the multiple x-ray energies necessary for processing of process block 72 for either industrial or medical imaging may include a standard x-ray tube 89, for example, having an anode and cathode accelerating electrons against a target to produce Bremsstrahlung radiation to provide multiple levels of radiation energy 90 by adjusting the voltage across the cathode and anode using an adjustable voltage power supply 92 providing energy to the x-ray tube 89. A fan beam or cone beam of x-rays may be produced.

Figure 6:
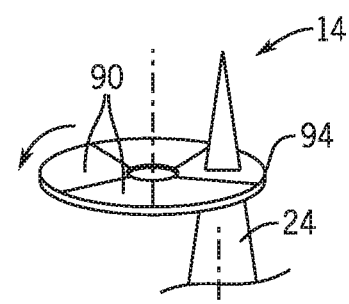
FIG. 6 is a simplified representation of a second embodiment of a multi-energy x-ray source employing a rotating filter wheel.

Referring to FIG. 6, in an alternative embodiment, a polychromatic x-ray source of any kind may be intercepted by a rotating filter wheel 94 having regions 96 with different filtration materials to provide for different spectra of polyenergetic x-ray radiation that may be used to acquire the images of different energies discussed herein.

Figure 7:
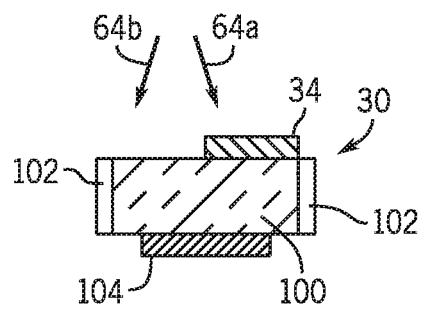
FIG. 7 is a cross-section along a plane of radiation of a detector element in a first embodiment employing a filter mask.

Referring now to FIG. 7, the detector elements 32 may be either direct or indirect x-ray detectors, for example, providing for a converter material 100 sensitive to x-rays separated by gutter material 102 into adjacent detector elements 32. The gutter material 102 may be reflective or blocking to prevent x-ray, light, or electron crosstalk between detector elements 32. Each detector element 32 is associated with a sensor 104 spanning substantially the entirety of the converter material 100 of the detector element 32.

In the case of a direct detector, the converter material 100 may, for example, be a semiconductor material receiving x-rays to produce electrons in whole pairs where the electrons are collected by a sensor 104 which is an electrode. With an indirect detector, the converter material may be a scintillator or the like producing light when energized by the x-ray, the light being detected by a photo sensor operating as the sensor 104. In one embodiment, a portion (for example, half of the area) of the front face of the detector element 32 facing the x-ray source 14 is covered with a thin filter material 34 to provide the necessary spatial encoding of energies per the analysis discussed above.

Figure 8:
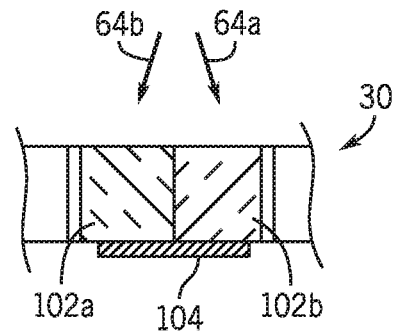
FIG. 8 is a figure similar to FIG. 7 showing a second embodiment employing different filter converter materials instead of a mask.

Referring now to FIG. 8 in an alternative embodiment, the filter may be provided by using two side by side different converter materials 102a and 102b having different sensitivities to x-ray energies as a function of energy. This approach can be used with either indirect or direct detectors.

Figure 9:
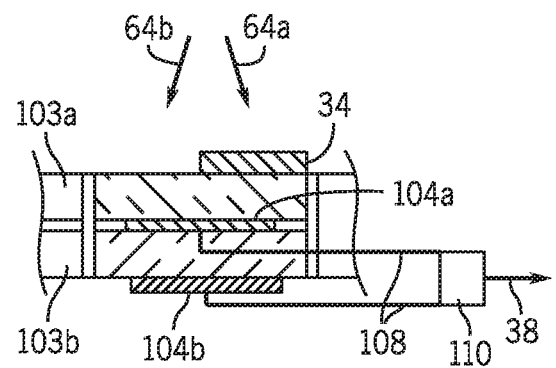
FIG. 9 is a figure similar to that of FIGS. 7 and 8 showing a stacked dual energy detector that may be used in the present invention.

Referring to FIG. 9, the invention also contemplates the possibility of an energy discriminating detector, either a single photon detector which can detect photon energies or, as shown, a stack detector having first and second converter materials 103a and 103 (or the identical converter material separated by a filters) arranged in series along the propagation direction of the x-rays. In this latter case, two different sensor panels 104a and 104b are used with respect to converter materials 103a and 103b to provide for two different signals along lines 108. Each of these different signals provides a different functional relationship between x-ray energy and the signal strength to provide energy discrimination. In one example, these two different signals may be combined by combiner 110 according to methods known in the art to produce a single signal that can be transmitted along signal lines 38 to provide both energy and fluence information. Again, a filter material 34 may be provided to encode a spatial position of received x-rays within the detector element 32 according to energy. On the other hand, using an energy discriminating detector means that the energy of the x-rays from the x-ray source 14 need not be varied. When the x-ray energy from the source 14 is held constant case, the analysis at process block 72 of FIG. 4 may be varied slightly as follows:

$$S_1 = \int_0^{E_{max}} dE\Omega(E)\omega(E)_1 [F(E)^L e^{-\int d\vec{l}^L \mu(x,y,E)} + F(E)^R e^{-\int d\vec{l}^R \mu(x,y,E)}] \quad (11)$$

$$S_2 = \int_0^{E_{max}} dE\Omega(E)\omega(E)_2 [F(E)^L e^{-\int d\vec{l}^L \mu(x,y,E)} + F(E)^R e^{-\int d\vec{l}^R \mu(x,y,E)}] \quad (12)$$

$$S_3 = \int_0^{E_{max}} dE\Omega(E)\omega(E)_3 [F(E)^L e^{-\int d\vec{l}^L \mu(x,y,E)} + F(E)^R e^{-\int d\vec{l}^R \mu(x,y,E)}] \quad (13)$$

$$S_4 = \int_0^{E_{max}} dE\Omega(E)\omega(E)_4 [F(E)^L e^{-\int d\vec{l}^L \mu(x,y,E)} + F(E)^R e^{-\int d\vec{l}^R \mu(x,y,E)}] \quad (14)$$

where the subscripts on $\omega(E)$ denote a detection of x-ray photons in different particular energy bands. Solving of the simultaneous equations again yields values of the line integrals or attenuation along sub-rays 64a and 64b.

The same analysis can be used, for example, with a photon counting device that is sensitive to different ranges of photon energy. The invention further contemplates that when multiple images are acquired, a combination of variations in x-ray energy from the x-ray source and energy detection discrimination may be used. For example, four unique measurements of S may be obtained using two different energy spectra $\Omega_1$ and $\Omega_2$ each using an energy discriminating detector w; with two energy thresholds j=1, 2 resulting in measurements $S_{1,1}$, $S_{1,2}$, $S_{2,1}$, and $S_{2,2}$.

It will be appreciated that portions of the various detector designs of FIGS. 7, 8, and 9 may be combined to similar effect, for example, replacing the filter material 34 in FIG. 9 with two converter materials per FIG. 8.

Figure 10:
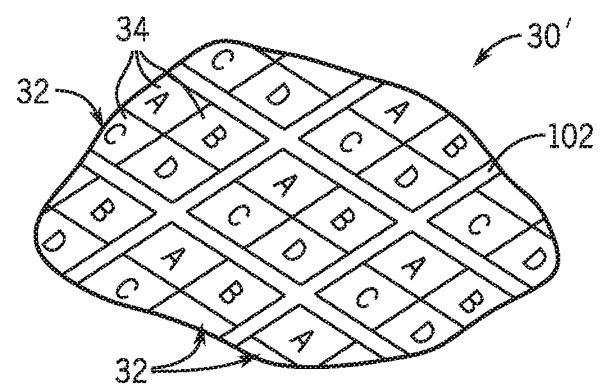
FIG. 10 is a perspective fragmentary view of a two-dimensional x-ray detector employing filters dividing each detector element into four portions.

Referring now to FIG. 10, the present invention can be expanded to a two-dimensional detector array 30 having detector elements 32 arranged, for example, in rows and columns across the surface of the detector array 30 extending perpendicularly to the axis of propagation of the x-rays. Each detector element 32 may be divided into quadrants (as opposed to halves preferred in the previous embodiments) each quadrant assigned to have a different filtration, for example, no filtration, and three additional filtrations represented by different filter materials 34, for example, Aluminum, Iodine, and Gadolinium. Each of the above examples describing a fan beam can instead use this two-dimensional detector array and an appropriate cone beam.

Figure 12:
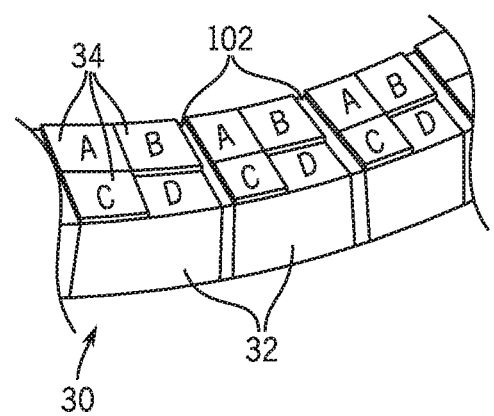
FIG. 12 is a fragmentary view of an alternative embodiment of the detector of FIG. 1 providing improved spatial resolution in two dimensions on a one-dimensional detector.

Referring to FIG. 12, it will be appreciated that this filter arrangement providing multiple filters (more than two) to each detector element 32 can be applied to a single dimensional detector array 30, for example, as previously discussed with respect to FIG. 1 or FIG. 3 to provide improved sampling resolution in two dimensions even for one-dimensional arrays. This can be used to provide improved resolution and helical, axial, step, or slot scanning of a volume using a one-dimensional detector.

As informed by the above discussion, for imaging of materials that are dominated by Compton scattering, this two-dimensional array will require four different images at different energy levels to extract the attenuation of rays received by these four different areas of the quadrant. When the material being analyzed includes significant photoelectric effect, eight different images at different energy levels will be required. More generally, when Compton scattering is the only interaction present, two measurements are required for one partition corresponding to two detector pixel portions. When photoelectric effects and Compton scattering must both be accounted for, measurements are required for one partition corresponding to two detector pixel portions. The number of independent measurements of S needed varies as a function of N*n where N is the number of photon matter interactions present in significant amounts and n is the number of pixel portions. This holds true for diagnostic imaging, which has significant photoelectric effect and Compton scattering, with small contributions from Rayleigh scattering that can be ignored, and the range below 1.022 MeV where Compton scattering is again dominant as well as above 1.022 MeV when pair production and Compton scattering are important.

Figure 11:
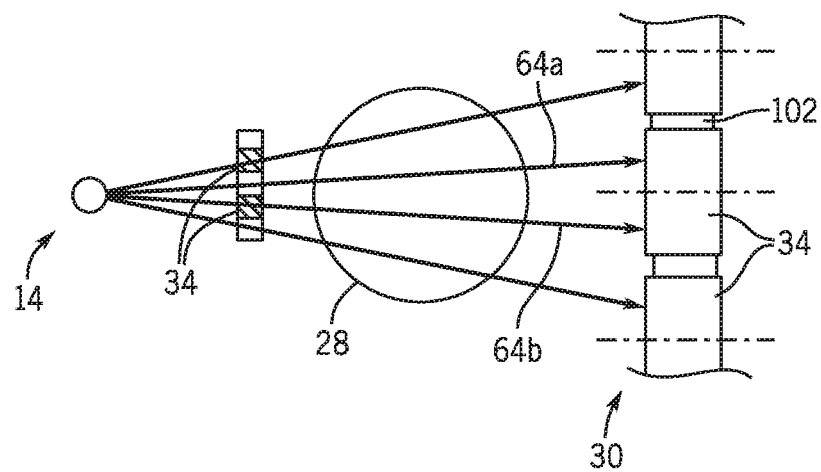
FIG. 11 is a figure similar to that of FIG. 2 showing an alternative filtering arrangement placing the filter near the x-ray source.

Referring now to FIG. 11, it will be appreciated that the filter material 34, for example, shown in FIG. 1 may be positioned not on the detector array 30 but between the x-ray source 14 and the imaged object 28 to similar effect. For example, filter materials 34 may be positioned adjacent to the x-ray source 14 spaced along the plane of the fan beam by apertures to intercept only one of sub-rays 64a or 64b. This approach would be expected to produce somewhat more blurring at the detector caused by the closeness of the focal spot, the latter having a finite and significant size with respect to the extent of filter material 34 in the fan beam plane. It will be appreciated that this filter material may be implemented in a checkerboard pattern of filter material 34 and apertures to provide filtration for a cone beam and two-dimensional detector array. The invention contemplates further that the x-ray source may be its own filter, controlling individual rays 64 to have different energy profiles, for example, with a steerable energy controlled beam, anode located filters, or the like.

As informed by the above discussion, the solution for each sub ray inherently involves solving for the photon-matter contributions from each physical effect. This means the methods discussed here simultaneously allow for sub pixel resolution and determination of the contributions for each detector portion from the underlying photon-matter interactions. For those skilled in the art, solving for these basic photon-matter interactions is commonly referred to as "spectral imaging" or when two interactions are solved, "dual energy imaging" with many applications in national security screening and medical imaging. For example, using this method, one may simultaneously create an iodine and a water basis map at a higher spatial resolution resolving between two different basis materials. Other pairs of basis materials can be distinguished in this way.

The term "different energies" as used herein refers generally to different distributions of x-ray energy at different energy levels and thus refers both to monochromatic x-rays having different monochromatic frequencies and polychromatic x-rays having the same or different frequency ranges but different shapes of fluence distribution. The terms "filtered" and "filter" should be understood to include mechanisms that operate to change the relative energy sensitivity of different portions of a detector element and not limited to only the portion of the detector element having an added filter. Thus, a filter may provide both an unfiltered portion and a filtered portion.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "controller" and "processor" should be understood to include one or more such devices that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What I claim is:

1. An x-ray imaging device comprising:
a multi-energy x-ray source providing first and second x-rays having different x-ray energies;
a multi-element x-ray detector positioned to receive the first and second x-rays from the multi-energy x-ray source after passage through an object to be imaged to provide an x-ray fluence output for each element;
an x-ray energy filter positioned with respect to the x-ray energy source and the multi-element x-ray detector to provide a first and second different response to at least one of the received first and second x-rays at different first and second portions of each element; and
a controller communicating with the multi-energy x-ray source and multi-element x-ray detector to:
(a) acquire a first and second x-ray image of x-ray fluence outputs of each of the elements of the multi-element x-ray detector at the first and second energy; and
(b) process the first and second x-ray images to provide independent fluence measurements for the first and second portions of each element of the multi-element x-ray detector.

2. The x-ray imaging device of claim 1 wherein the controller further (c) outputs an image having more than one independent pixel value for each given element of the multi-element x-ray detectors.

3. The x-ray imaging device of claim 1 wherein the processing of the first and second x-ray images uses a difference in fluence detected at given elements of the multi-element x-ray detector between different energies to deduce a relative proportion of x-ray fluence being received at the first and second portions of each element.

4. The x-ray imaging device of claim 1 wherein the multi-energy x-ray source provides at least a first, second, third, and fourth different energy and wherein the controller acquires a first, second, third, and fourth x-ray image of x-ray fluence outputs of each of the elements of the multi-element x-ray detector at the first, second, third, and fourth energy, respectively, to determine independent fluence measurements for the first and second portions of each element of the multi-element x-ray detector.

5. The x-ray imaging device of claim 1 wherein the multi-element x-ray detector provides elements distributed in two dimensions and wherein the x-ray energy filter provides a first, second, third, and fourth different response to a received x-ray's fluence at corresponding first, second, third, and fourth portions of each element and wherein the controller acquires a first, second, third, and fourth x-ray image of x-ray fluence outputs of each of the elements of the multi-element x-ray detector at the first and second energy and processes the first, second, third, and fourth x-ray images to provide independent fluence measurements for the first, second, third, and fourth of each element of the multi-element x-ray detector.

6. The x-ray imaging device of claim 1 wherein the multi-energy x-ray source switchably provides the first and second x-rays at different times.

7. The x-ray imaging device of claim 6 wherein the x-ray source is polychromatic in the first and second energy to represent different functions relating multiple energies of x-rays to different fluences for those energies.

8. The x-ray imaging device of claim 6 wherein the x-ray source is monochromatic and the first and second energy are different monochromatic x-ray energies.

9. The x-ray imaging device of claim 1 wherein the multi-energy x-ray source is polychromatic and the multi-element x-ray detector is an energy discriminating detector that can distinguish between different x-ray energies.

10. The x-ray imaging device of claim 1 wherein the x-ray filter is an absorbing material placed between the object to be imaged and the multi-element x-ray detector and covering only a portion of each element of the multi-element x-ray detector.

11. The x-ray imaging device of claim 1 wherein the x-ray filter is an absorbing material positioned between the multi-energy x-ray source and the object to be imaged to intercept only a portion of the x-rays received by each given element of the multi-element x-ray detector.

12. The x-ray imaging device of claim 1 wherein the x-ray filter provides the first and second different response by means of a first and second material converting x-ray energy to light energy or electric signal positioned at different portions of each detector element.

13. The x-ray imaging device of claim 1 wherein the x-ray output of each element of the multi-element x-ray detector provides a signal determined by a fluence of x-rays received over substantially an entire area of the element.

14. The x-ray imaging device of claim 1 wherein the x-ray filter provides a first, second, third, and fourth different response to a received x-ray's fluence at a corresponding first, second, third, and fourth portion of each element.

15. The x-ray imaging device of claim 14 wherein the multi-element x-ray detector provides elements distributed in only a single dimension and the first and second portions of each element are displaced with respect to the third and fourth portions of each element along the first axis substantially perpendicular to an axis of the x-rays and wherein the first and third portions are displaced with respect to the second and fourth portions along a second axis substantially perpendicular to the first axis and third axis of x-rays.

16. The x-ray imaging device of claim 1 further including a support supporting the multi-element x-ray detector, the multi-energy x-ray source, and the x-ray energy filter with respect to the object to be imaged to allow acquisition of a tomographic projection set at various angles with respect to the object to be imaged and wherein the controller further:
(c) acquires a first and second x-ray image of x-ray fluence outputs of each of the elements of the multi-element x-ray detector at the first and second energy; and
(d) processes the first and second x-ray images to provide independent fluence measurements for the first and second portions of each element of the multi-element x-ray detector.

17. The x-ray imaging device of claim 1 wherein the x-rays are selected from the group consisting of megavoltage voltage and kilovoltage x-rays.

18. The x-ray imaging device of claim 1 wherein the elements are selected from the group consisting of direct detectors having a single electrode associated with each detector element and indirect detectors having a single photo sensor associated with each detector.

19. The x-ray imaging device of claim 1 wherein the controller further
(c) processes the first and second x-ray images to distinguish between first and second basis materials of the object being imaged for each element of the multi-element x-ray detector.

* * * * *